United States Patent
Aubonnet et al.

(10) Patent No.: US 7,584,753 B2
(45) Date of Patent: Sep. 8, 2009

(54) DEMAND AND DILUTION MASK REGULATOR AND METHOD OF REGULATING ADDITIONAL OXYGEN IN THE MASK REGULATOR

(75) Inventors: Séverine Aubonnet, Viroflay (FR); Patrick Maire, Raizeux (FR); Didier Lamourette, Les Essarts le Roi (FR); Benoît Estaca Sagot, Levallois-Perret (FR)

(73) Assignee: Intertechnique (FR)

( * ) Notice: Subject to any disclaimer, the term of this patent is extended or adjusted under 35 U.S.C. 154(b) by 718 days.

(21) Appl. No.: 10/576,912

(22) PCT Filed: Jul. 15, 2004

(86) PCT No.: PCT/EP2004/009163

§ 371 (c)(1),
(2), (4) Date: Apr. 24, 2006

(87) PCT Pub. No.: WO2006/005372

PCT Pub. Date: Jan. 19, 2006

(65) Prior Publication Data

US 2007/0107729 A1    May 17, 2007

(51) Int. Cl.
*A61M 11/00*    (2006.01)

(52) U.S. Cl. .............. 128/204.25; 128/204.24; 128/204.18

(58) Field of Classification Search ........... 128/200.24, 128/206.27, 204.18, 204.19, 204.21–204.29, 128/205.11, 205.23, 205.24
See application file for complete search history.

(56) References Cited

U.S. PATENT DOCUMENTS

| 3,762,439 | A | 10/1973 | Heath |
| 4,336,590 | A | 6/1982 | Jacq et al. |
| 4,856,507 | A | 8/1989 | Ouillon et al. |
| 5,351,682 | A | 10/1994 | Foote |
| 6,796,306 | B2 * | 9/2004 | Martinez ............ 128/204.26 |
| 2003/0084901 | A1 * | 5/2003 | Martinez ............ 128/204.26 |

FOREIGN PATENT DOCUMENTS

WO   WO 03/039679   5/2003

* cited by examiner

*Primary Examiner*—Steven O Douglas
(74) *Attorney, Agent, or Firm*—Dean W. Russell; Kilpatrick Stockton LLP

(57) ABSTRACT

A demand and dilution mask regulator comprising an oxygen feed circuit and a dilution circuit for supplying air. The oxygen feed circuit and the dilution circuit are connected to a mixing chamber (35). In the dilution circuit, the inhaled breathe-in air flow rate is measured through a capillary duct (43) connected to a Venturi construction (41). A method of regulating the flow rate of additional oxygen uses flow rate data measured through the capillary duct (43) for controlling the oxygen flow rate to be supplied to the mixing chamber (35).

7 Claims, 2 Drawing Sheets

Figure 1:
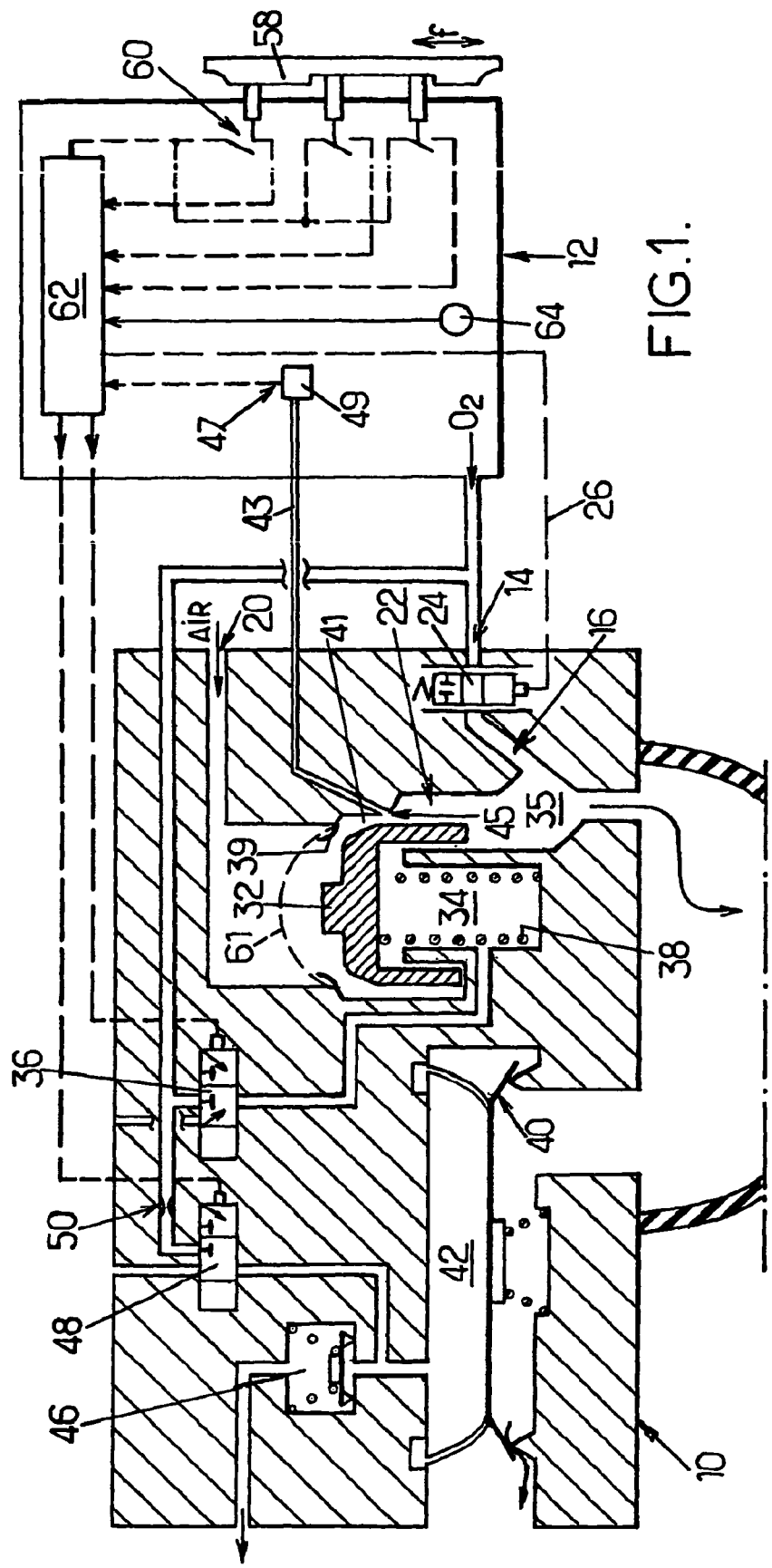

DEMAND AND DILUTION MASK REGULATOR AND METHOD OF REGULATING ADDITIONAL OXYGEN IN THE MASK REGULATOR

CROSS REFERENCE TO RELATED APPLICATIONS

This application is the U.S. national phase of International Application No. PCT/EP2004/009163 filed Jul. 15, 2004 published in English on Jan. 19, 2006 as International Publication No. WO 2006/005372 A1, the contents of which are incorporated by reference herein.

The present invention relates to demand and dilution mask regulators for breathing apparatuses for use by the crew of civil or military aircraft who, above a determined cabin altitude, need to receive breathing gas providing oxygen at least a minimum flow rate that is a function of altitude, or providing, on each intake of breath, a quantity of oxygen that corresponds to a minimum concentration for oxygen in the inhaled mixture. The minimum rate at which oxygen must be supplied is set by standards, and for civil aviation these standards are set by the Federal Aviation Regulations (FAR).

Attempts have been made to control additional oxygen flow in the inhaled mixture to come close to the flow rate that is actually needed. For example, the prior art document WO 03/039679 discloses a demand and dilution mask regulator comprising:
- an oxygen feed circuit connecting, through a first flow path, a pressurized inlet for oxygen coming from an oxygen source and admitted into a mixing chamber leading to a breathing mask, via an electrically-controlled valve for controlling the oxygen flow rate,
- a dilution circuit supplying air, through a second flow path, from an inlet connected to an air source, to an outlet leading to the mixing chamber.

In this prior art device, a pressure sensor that detects the drop in pressure in the dilution circuit is located near the mixing chamber. Therefore, when an intake of breath is inhaled, turbulences appear in the mixing chamber that disturb the pressure measured by said pressure sensor. Consequently, a safety margin has to be maintained between the minimum rate at which oxygen must be supplied and the oxygen flow rate actually supplied.

The present invention seeks in particular to provide a regulation device and method making it possible to cause the oxygen flow rate that is required from the source to come closer to the flow rate that is actually needed.

For this purpose, the invention provides a demand and dilution mask regulator according to claim 1.

The Venturi constriction amplifies the air inhaled breathe-in flow rate. Consequently, it can be more accurately measured. Further, since the pressure at the Venturi constriction is measured through the capillary duct, this measurement does not disturb the air flow rate through the Venturi constriction making the pressure measurement even more accurate. Recourse can also be made to one or several of the features according to claims 2 to 4.

According to another aspect, the invention relates to a breathing equipment according to claim 5.

According to yet another aspect, the invention relates to a method according to any one of claims 6 and 7.

Figure 2:
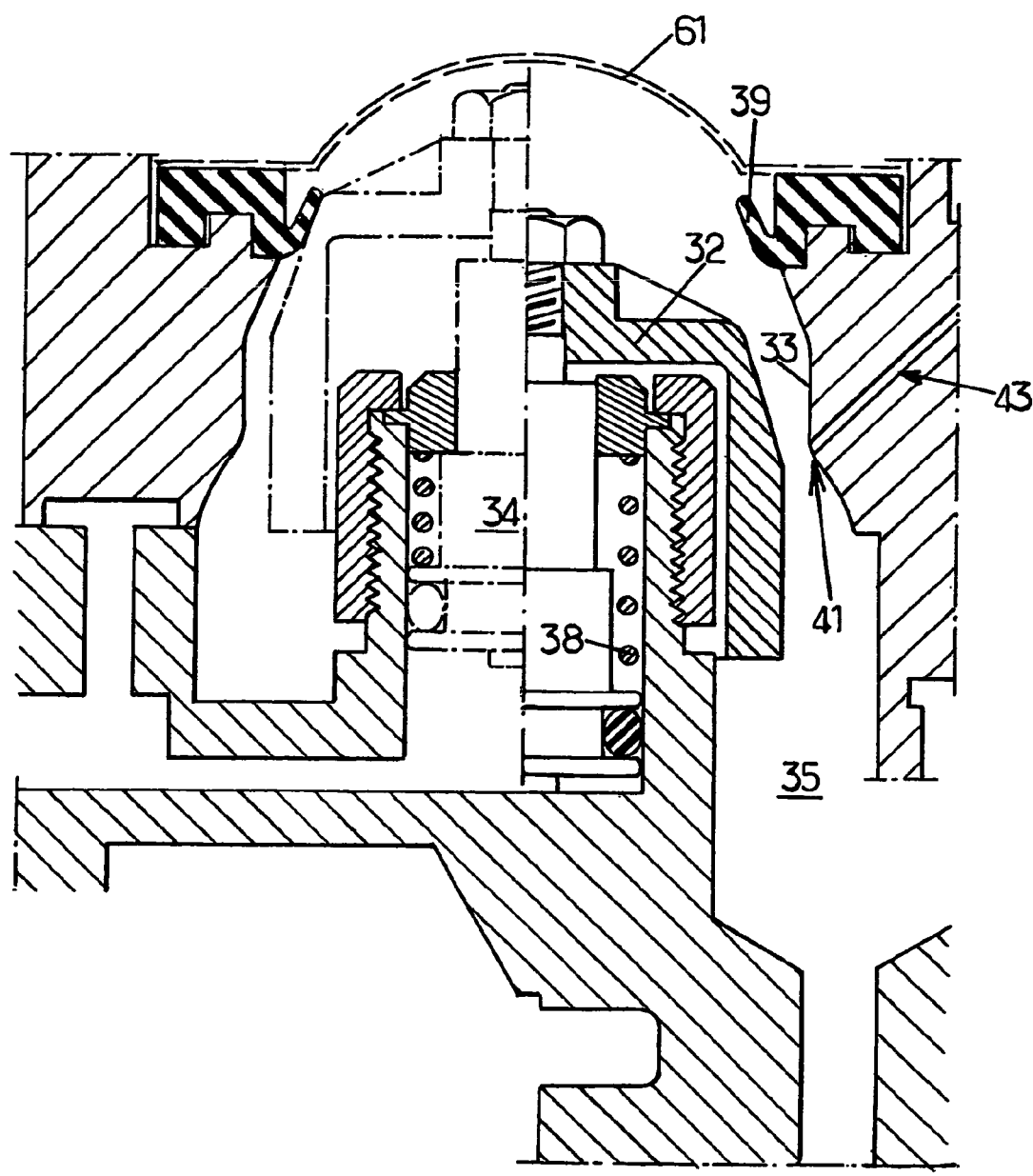

The above characteristics and others that can advantageously be used in association with preceding characteristics, but that can also be used independently, will appear better on reading the following description of particular embodiments, given as non-limiting examples. The description refers to the accompanying drawings, in which:

FIG. 1 is a pneumatic and electronic diagram showing the components involved by the invention in a regulator, and FIG. 2 is a diagrammatic view of enlarged part of FIG. 1.

The regulator shown in FIG. 1 comprises two portions, one portion 10 incorporated in a housing carried by a mask (not shown) and the other portion 12 carried by a box for storing the mask. The box may be conventional in general structure, being closed by doors and having the mask projecting therefrom. Opening the doors by extracting the mask causes an oxygen feed cock to be opened.

The portion carried by the mask is constituted by a housing comprising a plurality of assembled-together parts having recesses and passages formed therein for defining a plurality of flow paths.

A first flow path connects an inlet 14 for oxygen to an outlet 16 leading to the mask. A second path connects an inlet 20 for dilution air to an outlet 22 leading to the mask. The flow rate of oxygen along the first path is controlled by an electrically-controlled cock. In the example shown, this cock is a proportional valve 24 under voltage control connecting the inlet 14 to the outlet 16 and powered by a conductor 26. It would also be possible to use an on/off type solenoid valve, controlled using pulse width modulation at a variable duty ratio.

A "demand" subassembly is interposed on the direct path for feeding dilution air to the mask, said subassembly acting to suck in ambient air and to detect the instantaneous demanded flow rate.

In the example shown, the right section of the dilution air flow path is defined by an internal surface 33 of the housing, and the end edge of a piston 32 slidingly mounted in the housing. The piston is subjected to the pressure difference between atmospheric pressure and the pressure that exists inside a chamber 34. An additional electrically-controlled valve 36 (specifically a solenoid valve) serves to connect the chamber 34 either in the atmosphere or else to the pressurized oxygen feed. The electrically-controlled valve 36 thus serves to switch from normal mode with dilution to a mode in which pure oxygen is supplied (so-called "100%" mode). When the chamber 34 is connected to the atmosphere, a spring 38 holds the piston 32 on a seat 39 but allows the piston 32 to separate from the seat 39, when a user inhales an intake, in order to let air pass through the air flow path, in the mixing chamber 35 where air is mixed with oxygen. When the chamber 34 is connected to the oxygen supply the piston 32 presses against the seat 39, thereby preventing air from passing. The piston 32 can also be used as the moving member of a servo-controlled regulator valve. In general, regulators are designed to make it possible not only to perform normal operation with dilution, but also operation using a feed of expanded pure oxygen (so-called "100%" operation), or of pure oxygen at a determined pressure higher than that of the surrounding-atmosphere (so-called "emergency" operation) These abnormal modes of operation are required in particular when it is necessary to take account of a risk of smoke or toxic gas being present in the surroundings.

The terms "oxygen under pressure" or "pure oxygen" should be understood as covering both pure oxygen as supplied from a cylinder, for example, and air that is highly enriched in oxygen, typically to above 90%. Under such circumstances, the actual content of oxygen in the enriched air constitutes an additional parameter for taking into account, and it needs to be measured.

The air flow path comprises a Venturi constriction 41, between the piston 32 and the housing of the portion 10. The Venturi constriction 41 has, for example, a section of 0.57 mm². This section has been determined according to a particular mask model and can be changed for other mask models. A capillary duct 43 having an inlet port 45 is connected to the Venturi constriction 41 and an outlet port 47 is connected to a pressure sensor 49. The capillary duct 43 has a diameter of 0.3 mm. But this diameter can be varied between 0.1 and 0.4 mm. The pressure sensor 49 measures the air pressure in the Venturi constriction 41 through the capillary duct 43. The signal from the pressure sensor 49 is transmitted to an electronic circuit 62.

The housing of the portion 10 also defines a breathe-out path including a breathe-out valve 40. The shutter element of the valve 40 shown is of a type that is in widespread use at present for performing the two functions of acting both as a valve for piloting admission and as an exhaust valve. In the embodiment shown, it acts solely as a breathe-out valve while making it possible for the inside of the mask to be maintained at a pressure that is higher than the pressure of the surrounding atmosphere by increasing the pressure that exists in a chamber 42 defined by the valve 40 to a pressure higher than ambient pressure.

In a first state, an electrically-controlled valve 48 (specifically a solenoid valve) connects the chamber 42 in the atmosphere, in which case breathing out occurs as soon as the pressure in the mask exceeds ambient pressure. In a second state, the valve 48 connects the chamber 42 to the pressurized oxygen feed via a flow rate-limiting constriction 50. Under such circumstances, the pressure inside the chamber 42 takes up a value which is determined by a relief valve 46 having a rate closure spring.

The housing for the portion 10 may further carry means enabling a pneumatic harness of the mask to be inflated and deflated. These means are of conventional structure and consequently they are not shown nor described.

The portion 12 of the regulator which is carried by the mask storage box includes a selector 58 that is movable in the direction of arrow f and is suitable for being placed in three different positions by the user.

In the position shown in FIG. 1, the selector 58 closes a normal mode switch 60. In its other two positions, it closes respective switches for 100% mode and for emergency mode.

The switches are connected to the electronic circuit 62 which operates, as a function of the selected operating mode, in response to the cabin altitude as indicated by a sensor 64 and in response to the instantaneous flow rate being demanded as indicated by the pressure sensor 49 to determine the rate at which to supply oxygen to the wearer of the mask. The circuit card provides appropriate electrical signals to the first electrically-controlled valve 24.

In normal mode, the pressure sensor 49 supplies the instantaneous demand pressure to the outlet 22 from the air flow path, filtered through the filter 61, into the mask (see continuous line in FIG. 2). The electronic circuit 62 receives this signal together with information concerning the altitude of the cabin that needs to be taken into account and that comes from the sensor 64. The electronic circuit 62 then determines the quantity or flow rate of oxygen to be supplied using the following formula:

$$QATPO = K\sqrt{\frac{T}{1\tilde{P_A}}}\sqrt{\Delta P}$$

where
AP is the pressure measured by the pressure sensor 49 connected to the capillary duct 43,
$P_A$ is a pressure measured in the ambient atmosphere,
T is the temperature in Kelvin, and
K is a constant adjusted by the one skilled in the art according to altitude rate.

In 100% mode, i.e. when the wearer of the mask moves the selector on notch downwards from the position shown in FIG. 1, the electronic circuit 62 applies an electrical reference signal to the electrically-controlled valve 36. This causes the chamber 34 to be pressurized, pressing the piston 32 against the seat 39 and closing off the dilution air inlet (see dashed lines in FIG. 2). The pressure sensor 49 detects the drop in pressure in the ambient air inlet circuit and delivers corresponding information to the electronic circuit 62. The electronic circuit 62 then determines the oxygen flow rate to be delivered. The first electrically-controlled valve 24 then delivers the computed quantity of oxygen to the wearer of the mask.

When the wearer selects "emergency" mode by moving the selector 28 further downwards, the electronic circuit 62 delivers an electrical reference to the electrically-controlled valve 48, which then admits pressure into the chamber 42, which pressure is limited by the release valve 46. As a general rule, the positive pressure that is established is about 5 millibars (mbar). Simultaneously, the dilution air inlet is interrupted as before. The pressure sensor 49 still delivers a signal to the electronic circuit 62 which determines the quantity of oxygen that needs to be supplied in order to bring the pressure in the air inlet circuit up to a value equal to the rated value of the release valve 46.

The invention claimed is:
1. A demand and dilution mask regulator comprising:
an oxygen feed circuit connecting, through a first flow path, a pressurized inlet for oxygen coming from an oxygen source and admitted into a mixing chamber leading to a breathing mask, via an electrically-controlled valve for controlling the oxygen flow rate,
a dilution circuit supplying air, through a second flow path, from an inlet connected to an air source, to an outlet leading to the mixing chamber, characterized in that the second flow path comprises a Venturi constriction and a capillary duct having an inlet port connected to the Venturi constriction and an outlet port connected to a pressure sensor.
2. A regulator according to claim 1, wherein the capillary duct has a diameter comprised between 0.1 and 0.4-mm.
3. A regulator according to claim 1, wherein the Venturi constriction has a section of essentially 0.57 mm².
4. A regulator according to claim 1, wherein the inlet port of the capillary duct is located upstream of the mixing chamber.
5. A protective breathing equipment with a mask comprising a regulator according to claim 1 and a mask storage box comprising an electronic control circuit and the pressure sensor, the capillary duct, electric wires and an oxygen duct extending from the mask storage box to the regulator.

6. A method of regulating a flow rate of additional oxygen taken from a pressurized inlet for oxygen coming from a source and admitted, through a first flow path, into a mixing chamber leading to a breathing mask, via an electrically-controlled valve for controlling the oxygen flow rate, the method comprising supplying air, through a second flow path, from an inlet connected to an air source, to an outlet leading to the mixing chamber, the method being characterized in that it further comprises:
- measuring the air pressure in the second flow path at a Venturi constriction, through a capillary duct having an inlet port connected to the Venturi constriction and an outlet port connected to a pressure sensor, and
- using data from the pressure sensor for controlling the oxygen flow rate delivered through the electrically-controlled valve.

7. A method according to claim 6, wherein the oxygen flow rate delivered through the electrically-controlled valve is given by:

$$Q_{ATPD} = K\sqrt{\frac{T}{P_A}}\sqrt{\Delta P}$$

where
- $\Delta P$ is the pressure measured by the pressure sensor connected to the capillary duct,
- $P_A$ is a pressure measured in the ambient atmosphere,
- T is the temperature in Kelvin, and
- K is a constant adjusted according to altitude rate.

* * * * *

UNITED STATES PATENT AND TRADEMARK OFFICE
CERTIFICATE OF CORRECTION

| | | |
|---|---|---|
| PATENT NO. | : 7,584,753 B2 | |
| APPLICATION NO. | : 10/576912 | |
| DATED | : September 8, 2009 | |
| INVENTOR(S) | : Aubonnet et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 807 days.

Signed and Sealed this

Fourteenth Day of September, 2010

David J. Kappos
*Director of the United States Patent and Trademark Office*